United States Patent
Koch et al.

(10) Patent No.: US 6,455,530 B1
(45) Date of Patent: *Sep. 24, 2002

(54) 2R,4S,S,S- AND 2S,4R,S,S-HYDROXYITRACONAZOLE

(75) Inventors: Patrick Koch, Marlborough; John R. McCullough, Worcester; Chris H. Senanayake, Shrewsbury; Gerald J. Tanoury, Marlborough; Yaping Hong, Framingham, all of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/663,992

(22) Filed: Sep. 18, 2000

Related U.S. Application Data

(63) Continuation of application No. 09/304,483, filed on May 3, 1999, now abandoned, which is a continuation of application No. 08/968,640, filed on Nov. 12, 1997, now abandoned
(60) Provisional application No. 60/031,073, filed on Nov. 12, 1996.

(51) Int. Cl.[7] ..................... A61K 31/496; C07D 405/14
(52) U.S. Cl. ................. 514/254.07; 514/85; 544/337; 544/366
(58) Field of Search ................. 544/366, 337; 514/85, 254.07

(56) References Cited

U.S. PATENT DOCUMENTS

| | | | |
|---|---|---|---|
| 4,267,179 A | 5/1981 | Heeres et al. | 424/25 D |
| 4,338,327 A | 7/1982 | Heeres et al. | 424/269 |
| 4,352,808 A | 10/1982 | Rane et al. | 424/258 |
| 4,402,956 A | 9/1983 | Silvestrini et al. | 424/250 |
| 4,791,111 A | 12/1988 | Heeres et al. | 514/252 |
| 4,859,670 A | 8/1989 | Kampe et al. | 514/252 |
| 4,916,134 A | 4/1990 | Heeres et al. | 514/252 |
| 4,931,444 A | 6/1990 | Van Wauwe et al. | 514/252 |
| 5,474,997 A | 12/1995 | Gray et al. | 514/252 |
| 5,661,151 A | 8/1997 | Saksena et al. | 514/252 |
| 5,693,626 A | 12/1997 | Saksena et al. | 514/85 |
| 5,703,079 A | 12/1997 | Saksena et al. | 514/252 |
| 5,703,236 A | 12/1997 | Saksena et al. | 544/366 |
| 5,707,977 A | 1/1998 | Heeres et al. | 514/85 |
| 5,710,154 A | 1/1998 | Saksena et al. | 514/252 |
| 5,714,490 A | 2/1998 | Saksena et al. | 514/252 |
| 5,952,502 A * | 9/1999 | McCullough et al. | 544/337 |
| 6,147,077 A * | 11/2000 | Koch et al. | |

FOREIGN PATENT DOCUMENTS

| | | |
|---|---|---|
| WO | WO 93/19061 | 9/1993 |
| WO | WO 95/17407 | 6/1995 |
| WO | WO 95/19983 | 7/1995 |
| WO | WO 96/29325 | 9/1996 |

OTHER PUBLICATIONS

Saksena et al., "Concise Asymmetric Routes to 2,2, 4–Trisubstituted Tetrahydrofurans Via Chiral Titanium Imide Enolates: Key Intermediates Towards Synthesis of Highly Active Azole Antifungals SCH 51048 and SCH 56592", Tetrahedron Letters, 37, No. 32, 5657–5660, 1996.

* cited by examiner

*Primary Examiner*—Emily Bernhardt
(74) *Attorney, Agent, or Firm*—Heslin Rothenberg Farley & Mesiti PC; Candice J. Clement, Esq.

(57) ABSTRACT

A method of preparation of optically pure isomers of hydroxyitraconazole, in particular the two cis dioxolane diastereomers of the sec-butyl (S,S)-isomer, and to phosphate and sulfate derivatives thereof is disclosed. Pharmaceutical compositions containing these compounds and to their use for the treatment of fungal infection are also disclosed.

4 Claims, No Drawings

2R,4S,S,S- AND 2S,4R,S,S-HYDROXYITRACONAZOLE

CROSS REFERENCE TO RELATED APPLICATIONS

This application is a continuation of U.S. patent application Ser. No. 09/304,483, filed May 3, 1999 as a continuation of U.S. patent application Ser. No. 08/968,640, now abandoned, filed Nov. 12, 1997 and claims the priority of U.S. Provisional Patent Application Serial No. 60/031,073 filed Nov. 12, 1996. The entire disclosures of the prior applications are incorporated herein by reference.

FIELD OF THE INVENTION

The present invention relates to a method of preparation of optically pure isomers of hydroxyitraconazole, in particular the two cis dioxolane diastereomers of the sec-butyl (S,S)-isomer, and to phosphate and sulfate derivatives thereof The invention also relates to pharmaceutical compositions containing these compounds and to their use for the treatment of fungal infection.

BACKGROUND OF THE INVENTION

Itraconazole, a well-known antifungal agent, is defined in the USAN and USP Dictionary of Drug Names as 4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4dihydro-2-(1-methylpropyl)-3H-1,2,4triazol-3-one or alternatively as (±)-1-sec-butyl-4[p-[4-[p-[[(2R*,4S *)-2-(2,4-dichlorophenyl)-2-(1H-1,2,4triazol-1-ylmethyl)-1,3-dioxolan-4-yl]methoxy]phenyl]-1-piperazinyl]phenyl]-Δ²-1,2,4-triazolin-5-one. The commercially available material is the cis isomer in the dioxolane ring and is represented by the structural formula I:

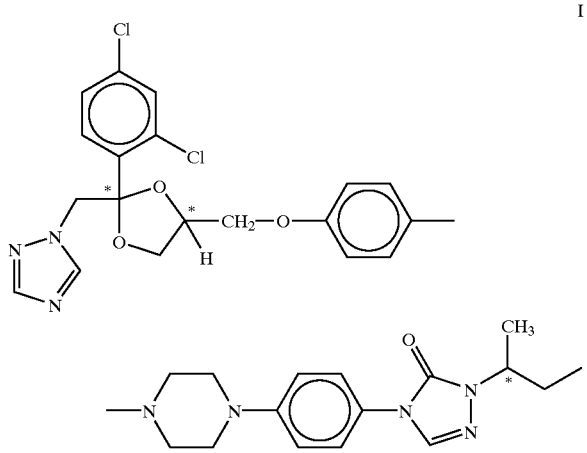

It will be noted that there are three asymmetric carbons in formula I (denoted by asterisks): two in the dioxolane ring and one in the sec-butyl side chain on the triazolone. There are eight possible isomers of a structure having three asymmetric carbons: (R,O,R), (R,R,S), (R,S,S), (S,S,S), (R,S,R), (S,R,S), (S,R,R) and (S,S,R). Because the commercially available itraconazole is a cis isomer, it comprises a mixture of only those isomers that describe a cis relationship in the dioxolane ring. Adopting the convention that the first denoted chiral center is at C-2 of the dioxolane ring, the second is at C-4 of the dioxolane and the third is in the sec-butyl group, commercial itraconazole is a mixture of (R,S,S), (R,S,R), (S,R,S) and (S,R,R) isomers. Compounds of this invention have the (2R,4S) and (2S,4R) configurations in the dioxolane ring.

The hydroxylation of the methylene carbon of the sec-butyl side chain creates an additional chiral center and gives rise to eight additional possible enantiomers. The compounds of the present invention are those in which the two asymmetric centers in the butyl chain are S (at the α carbon) and S (at the β carbon).

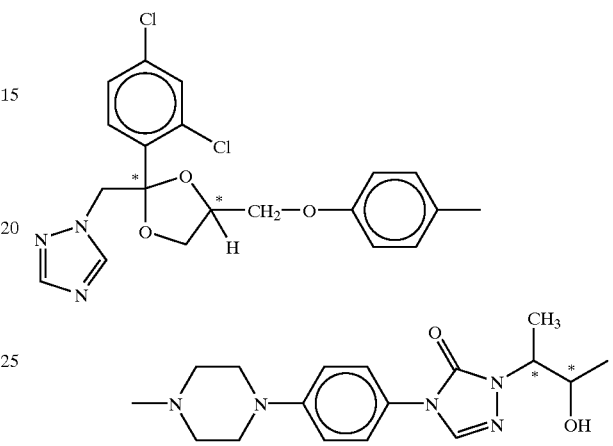

The graphic representations of racemic, ambiscalemic and scalemic or enantiomerically pure compounds used herein are taken from Maehr J. Chem. Ed. 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, among the structures below, those having open wedges are intended to encompass both of the pure enantiomers of that pair, those having solid wedges are intended to encompass the single, pure enantiomer having the absolute stereochemistry shown.

Itraconazole is an orally active, broad-spectrum antifungal agent and is structurally related to miconazole and clotrimazole. It impairs the synthesis of ergosterol, which is the principal sterol of fungal cell membranes. This presumably results in an increased permeability and leakage of intracellular content. At high concentration, cellular internal organelles involute, peroxisomes increase, and necrotic changes occur.

Following oral administration, itraconazole is slowly absorbed. Peak plasma levels are attained after 15 days of daily administration, and the pharmacokinetic behavior of itraconazole is nonlinear. The compound is eventually metabolized through the biologically active hydroxyitraconazole to several inactive metabolites. Metabolism is apparently through hepatic mechanisms, and in most subjects no metabolites are excreted in the urine [see, Hardin et al., Antimicro. Agents and Chemotherapy 32, 1310–1313 (1983)].

The racemic mixture of itraconazole has been approved for use as an antifungal agent for blastomycosis and histoplasmosis. The compound is also being investigated for use in aspergillosis, coccidioidomycosis, cryptococcosis, onychomycosis, dermatophyte and candidiasis infections.

Systemic fungal diseases (systemic mycoses) are usually chronic, very slowly developing conditions induced by opportunistic causative fungi which may not normally be pathogenic. However when they enter a host compromised by HIV, ionizing irradiation, corticosteroids, immunosuppressives, etc. or by such conditions as emphysema, bronchiectasis, diabetes mellitus, leukemia, burns and the like, they may become pathogenic. Symptoms in such fungal diseases are generally not intense, and may include fever, chills, anorexia and weight loss, malaise, and depression. Fungal diseases are often confined to typical anatomic distributions, and many involve a primary focus in the lung, with more characteristic manifestations of specific fungal infections when the fungus disseminates from a primary focus. For example, coccidioidomycosis occurs in a primary form as an acute, benign, self-limiting respiratory disease, with progressive disease developing from the primary form as a chronic, often fatal infection of the skin, lymph glands, spleen and liver. Similarly, blastomycosis primarily involves the lungs, and occasionally spreads to the skin. Other infectious diseases such as paracoccidioidomycosis and candidiasis offer a different course, and depending on the etiology may exhibit several forms involving the skin, mucous membranes, lymph nodes, and internal organs.

Superficial fungal infections are caused by dermatophytes or fungi that involve the outer layers of the skin, hair or nails. The infections may result in a mild inflammation, and cause intermittent remissions and exacerbations of a gradually extending, scaling, raised lesion. Yeast infections including candidiasis, and oral candidiasis (thrush) are usually restricted to the skin, and mucous membranes, and the symptoms vary with the site of infection.

Adverse effects associated with the administration of itraconazole include hepatotoxicity and inhibition of drug metabolism in the liver, leading to numerous, clinically significant, adverse drug interactions. [See, Gascon and Dayer *Eur. J. Clin. Pharmacol.* 41, 573–578 (1991) (interaction with midazolam); Honig et al. *J. Clin. Pharmacol.* 33, 1201–1206 (1993) (interaction with terfenadine); and Neuvonen et al. *Clin. Pharmacol. Therap.* 60, 54–61 (1996) (interaction with lovastatin).] Hypersensitivity reactions including urticaria and elevations in serum liver enzymes are also associated with the administration of the drug. Hepatoxicity is a less common but more serious adverse effect. Indeed, the use of oral conazoles as first line antifungals is usually discouraged because of the potentially serious consequences of the low incidence of hepatotoxicity [See, e.g., Lavrijsen et al. *Lancet* 340, 251–252 (1992)].

We have found evidence in our own studies in isolated guinea pig and rabbit hearts that the administration of racemic conazoles may be associated with an increased risk of cardiac arrhythmia. Arrhythmia has not been heretofore reported as a side effect of systemic itraconazole, although a particular subtype of arrhythmia, Torsades de Pointes, has been reported when racemic itraconazole was administered concurrently with terfenadine [Pohjola et al. *Eur. J. Clin. Pharmacol.* 45, 191–193 (1993)]. The lack of clinical reports of arrhythmia or QT anomalies may simply be a reflection of the fact that there is to date a relatively small subject population.

The relative non-polarity and insolubility of itraconazole give rise to two other drawbacks: it cannot be readily formulated in parenteral solution and it does not penetrate the blood-brain barrier. As a result, numerous therapeutic indications which require rapid achievement of efficacious blood levels or access to the CNS are beyond treatment with itraconazole. In particular, central candidiasis, which may be responsible for AIDS related dementia, cannot be treated with itraconazole.

Thus it would be particularly desirable to find a compound with the advantages of itraconazole which would not have the aforementioned disadvantages.

SUMMARY OF THE INVENTION

The compounds and compositions of the invention possess potent activity in treating local and systemic fungal, yeast and dermatophyte infections while avoiding adverse effects associated with the administration of itraconazole. The compounds and compositions of the invention also enjoy the particular advantage of being much more soluble in physiologically compatible solutions than is itraconazole. The preparation, for the first time, of the individual enantiomers of hydroxyitraconazole permits the preparation of unusually soluble single enantiomers and derivatives thereof.

In one aspect the invention relates to substantially pure single enantiomers of a compound of formula:

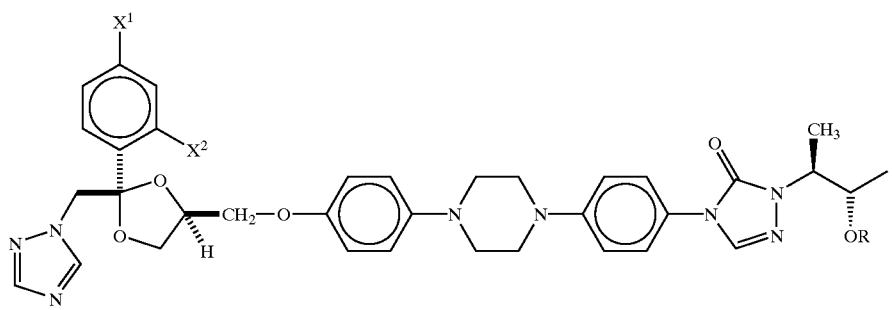

wherein $X^1$ and $X^2$ are independently chlorine or fluorine and R is hydrogen, —P(O)(OH)$_2$ or —SO$_3$H, or a salt thereof There are two such possible single enantiomers, represented by the formulae A and B:

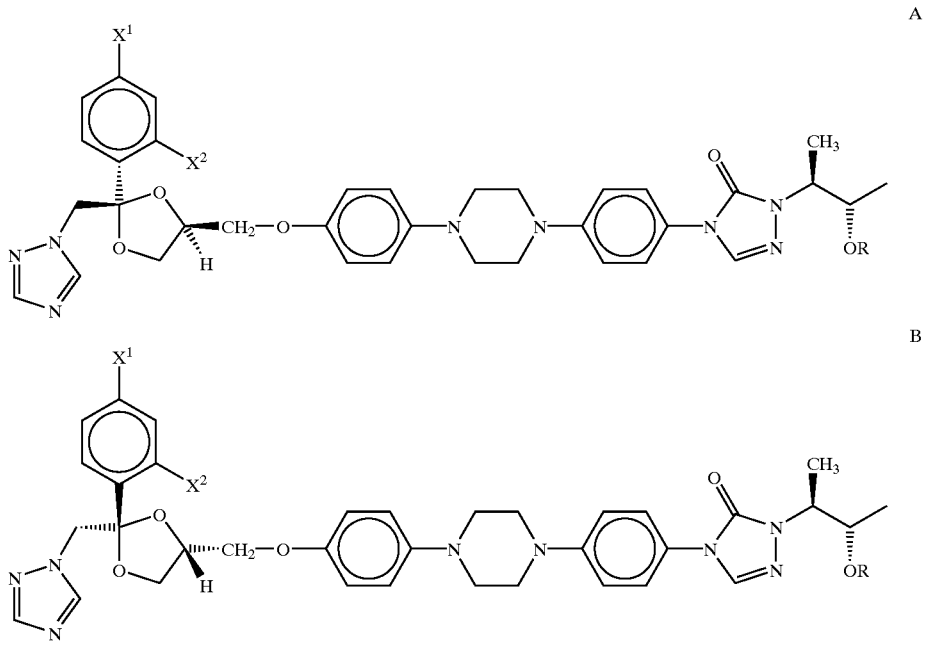

In another aspect the invention relates to pharmaceutical compositions comprising the compounds above and a pharmaceutically acceptable carrier. The compositions contain less than 10% by weight of other enantiomers or diastereomers having the same structural formula. Preferably, the compositions contain a single enantiomer A or B.

In another aspect, the invention relates to a method for treating or preventing fungal infection comprising administering to a mammal suffering from (or at risk from) a fungal infection a therapeutically effective amount of the above compounds.

In another aspect, the invention relates to a process for preparing a 2,4-disubstituted 3H-1,2,4triazol-3-one of formula

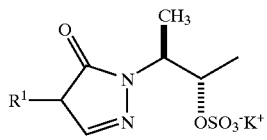

wherein $R^1$ is aryl or substituted aryl. The process comprises reacting a 2-aryl-3H-1,2,4-triazol-3-one of formula

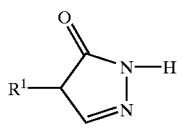

with a cis 4,5-dimethyl-1,2,3-dioxathiolane 2,2-dioxide of formula

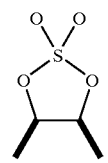

by forming the potassium salt of said 2-aryl-3H-1,2,4triazol-3-one with an excess of potassium hydride in an inert solvent in the presence of at least one equivalent of 1,4,7,10,13,16-hexaoxocyclooctadecane (18-crown-6) and adding said dioxathiolane at −5° C. to 25° C. For the synthesis of itraconazole enantiomers, $R^1$ is preferably

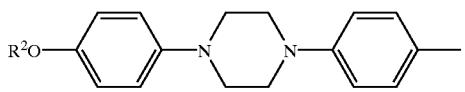

wherein $R^2$ is methyl or benzyl.

In another aspect, the invention relates to a process for preparing a dioxolane tosylate of formula

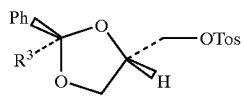

wherein Ph is phenyl or substituted phenyl, Tos is toluenesulfonyl and $R^3$ is heterocyclylmethyl. The process comprises the sequential steps of (a) dissolving a ketone of formula $R^3C(O)$ Ph and about one equivalent of an optically active 1,2-dihydroxypropyl toluenesulfonate in an inert solvent; (b) cooling to a temperature below 15° C.; (c) adding an excess of trifluoromethanesulfonic acid at <15° C.; (d) allowing the foregoing materials to react to form a ketal; and (e) introducing said ketal in solution into an excess of alkali metal carbonate or bicarbonate in water at 0 to 10° C.

DETAILED DESCRIPTION OF THE INVENTION

The compounds of the invention are synthesized by the general route shown in Schemes 1, 2, 3 and 4:

Scheme 1

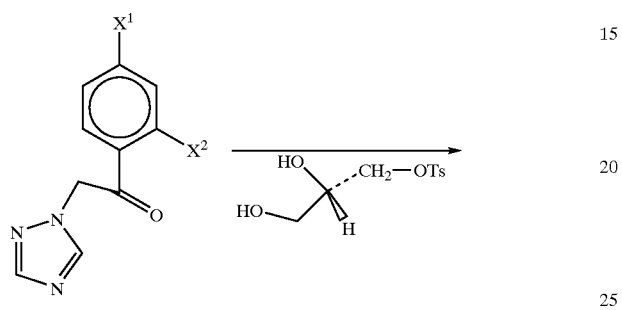

-continued

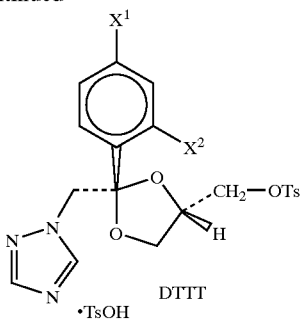

Scheme 2

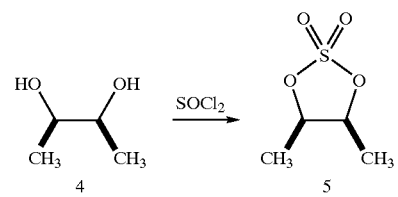

Scheme 3

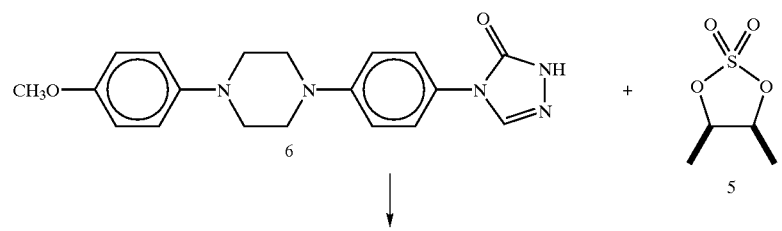

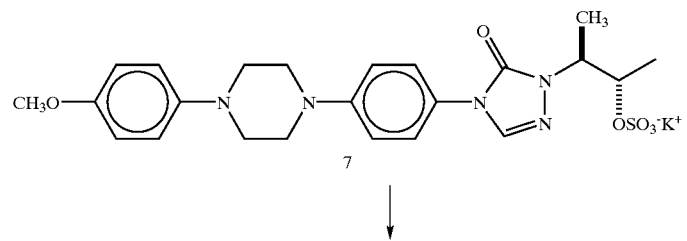

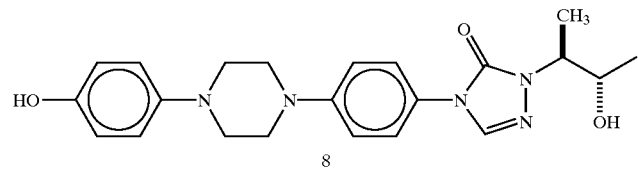

Scheme 4

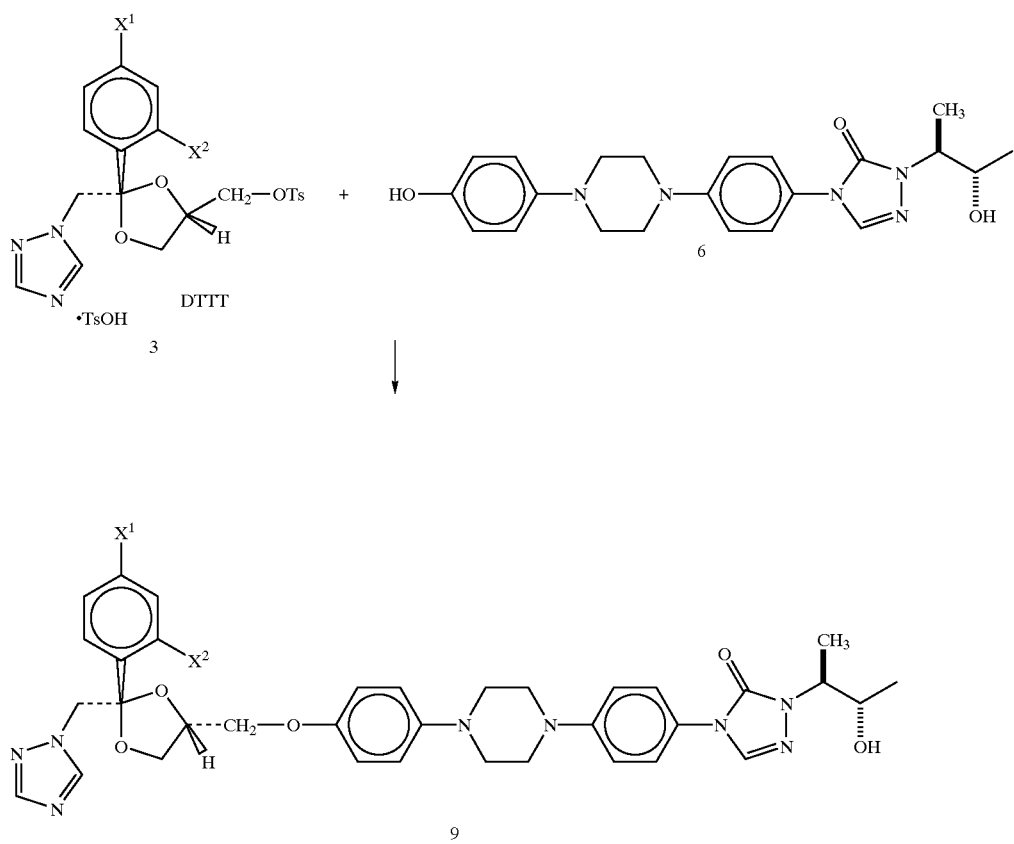

As shown in Scheme 1, the chiral dioxolane DTTT (3) is prepared by a literature method from threo-tosyloxy-1,2-propanediol by acid-catalyzed ketalization to provide DTT.

As shown in Scheme 2, the dioxothiolane 5 is prepared from a butanediol of appropriate configuration by treatment with thionyl chloride, followed by in situ oxidation of the resulting cyclic sulfite with sodium periodate in the presence of ruthenium trichloride.

As shown in Scheme 3,2,4-dihydro-4-[4-[4-(4-methoxyphenyl)-piperazinyl]phenyl]-3H-1,2,4-triazol-3-one (6), prepared by the method of example XVII in U.S. Pat. No. 4,267,179, is reacted with the dioxothiolane 5, prepared by the procedure of Gao and Sharpless [*J. Am. Chem. Soc.* 110, 7538 (1988)], using potassium hydride in DMF in the presence of crown ether. The resulting methoxy-sulfate salt is cleaved to the phenol-alcohol 8 by heating with 48% HBr at 100–110° C.

As shown in Scheme 4, the tosyl ester 3 from Scheme 1 and the phenol-alcohol 8 from Scheme 3 are reacted in the presence of potassium hydroxide in DMF to provide the product 9.

When it is desired that R in A or B be sulfate, the order of steps in Schemes 3 and 4 can be rearranged so that the methoxyl of 6 is cleaved before the addition of the residue of the sec-butyl side chain, and instead, 3 is added first, then 5.

When it is desired that R in A or B be phosphate, 8 is treated first with t-butyldimethylsilyl chloride and diisopropylethylamine to protect the phenol, then with dibenzyl diisopropylphosphoramidite and t-butylhydroperooxide according to the procedure of PCT application WO94/17407, which is incorporated herein by reference, to phosphorylate the alcohol. The silyl protecting group is removed with anhydrous tetrabutylammonium fluoride and the benzyl-protected phosphate is coupled with the doxolane tosylate as in Scheme 3. The benzyl protecting groups are cleaved by hydrogenolysis in the presence of a palladium catalyst to provide the phosphate product.

It will be noted that in the above Scheme 3 a racemic mixture of the RR and SS enantiomers of 8 is formed. The racemic mixture can be readily separated by chromatography on a chiral medium by methods well known in the art. Alternatively, single enantiomers can be produced by two different modifications of Scheme 3, shown in Schemes 5, 6 and 7:

Scheme 5
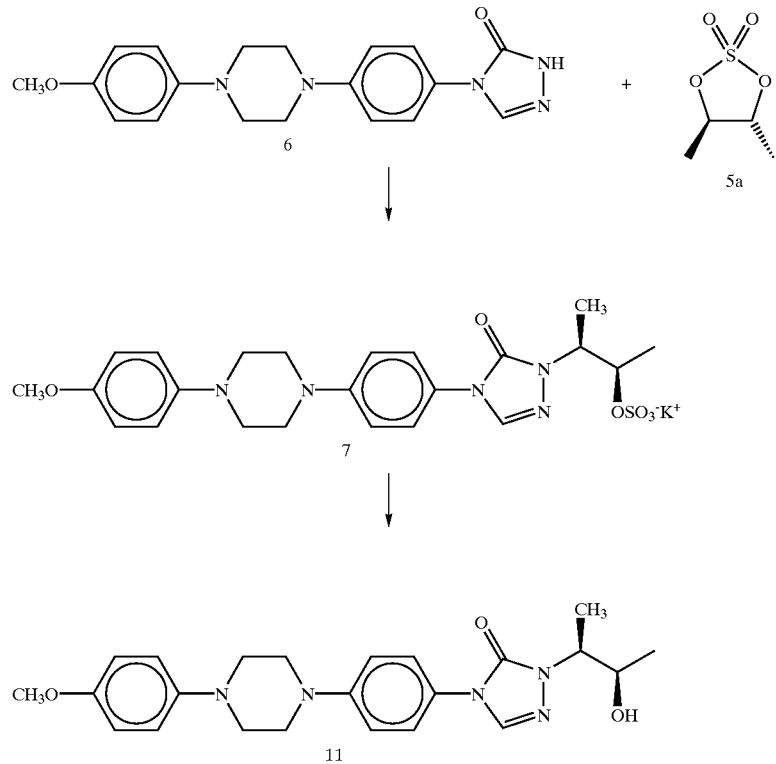
Scheme 6
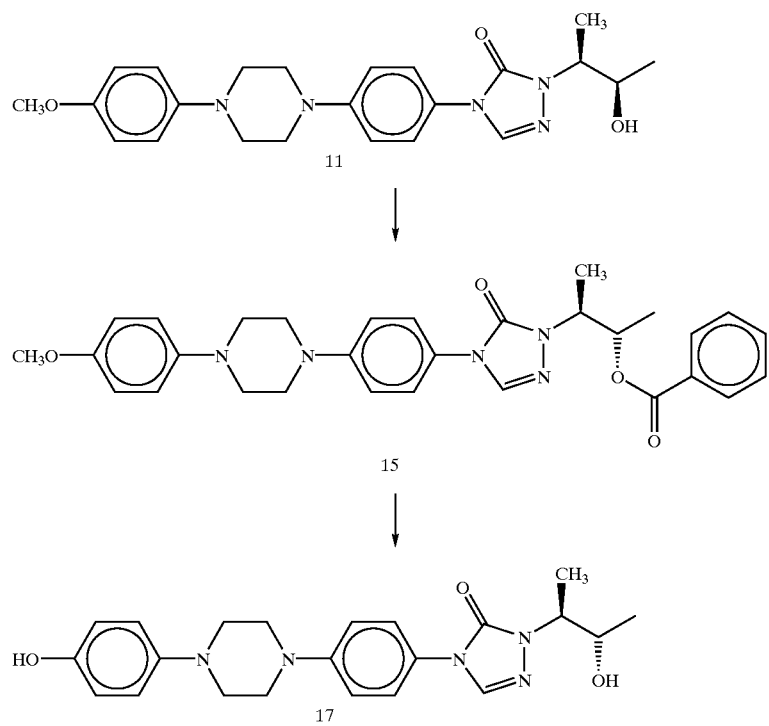

Scheme 7

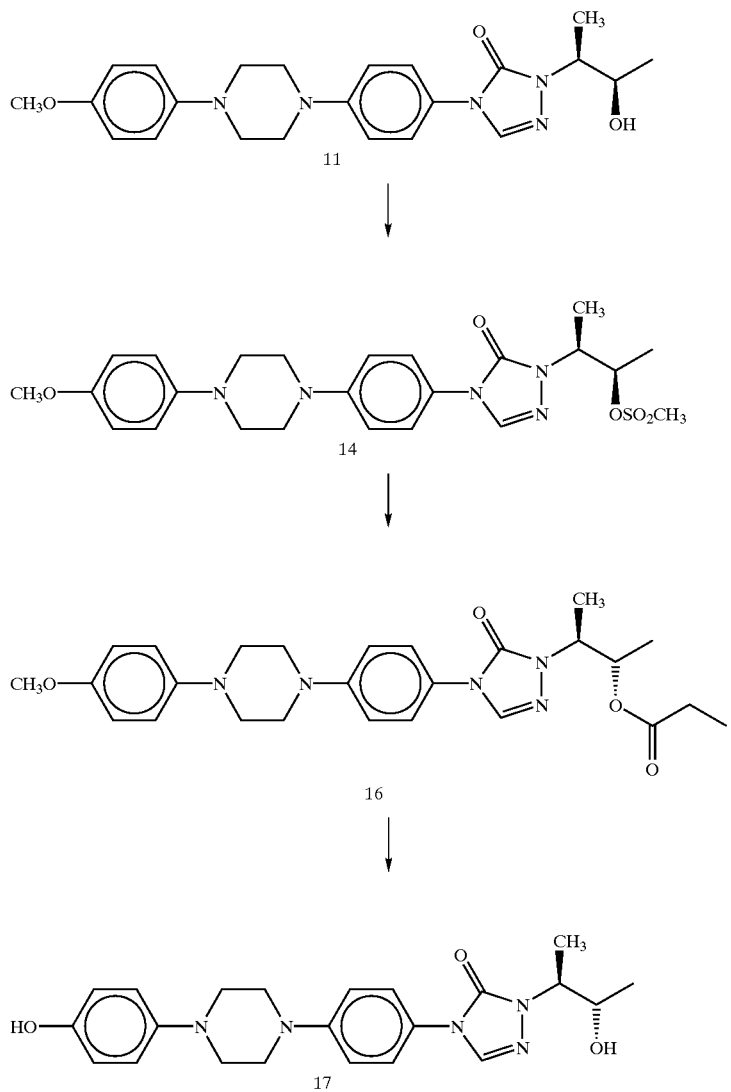

2,4-Dihydro-4-[4-[4-(4-methoxyphenyl)-piperazinyl]phenyl]-3H-1,2,4-triazol-3-one (6) is reacted with the dioxothiolane 5a as described for Scheme 3, but the sulfate ester of the resulting methoxy-sulfate salt is hydrolyzed without cleaving the methyl from the phenol by heating with 48% HBr at 45–50° C. to produce alcohol 11. As shown in Scheme 6, alcohol 11 may be treated with diisopropylazodicarboxylate, triphenylphosphine and benzoic acid according to the method of Mitsunobu [*Synthesis* 1981, 1–27], hydrolysed with potassium hydroxide in methanol, and cleaved with 48% HBr at reflux to provide 17, the single enantiomer of 8. Alternatively, as shown in Scheme 7, the alcohol 11 may be treated with methanesulfonyl chloride in the presence of dimethylaminopyridine and diisopropylethylamine and the resulting mesylate ester of 14 inverted by treatment with cesium propionate according to the method of Senanyake et al. [*Tet. Lett*. 34, 2425 (1993)] to provide the propionate ester 16. The methoxy-ester 16 may be cleaved as before with potassium hydroxide and then HBr to give 17.

Preparation of (−)-(2R,4S)-2-(2,4-Dichlorophenyl)-2-(1H-1,2,4-triazol-1-ylmethyl)-4-tosyloxymethyl-1,3-dioxolane Tosylate DTTT (3a Tosylate Salt)

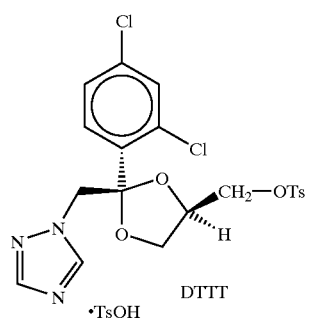

A suspension of (R)-tosyloxy-1,2-propanediol (10.0 g, 40 mmol) and 1-(2,4-dichlorophenyl)-2-(1H-1,2,4-triazol-1-yl)ethanone (10.0 g, 39 mmol) in toluene (50 mL) is cooled to 5° C., Triflic acid (15 mL, 4 eq) is slowly added so that the temperature stays below 15° C. After complete addition the reaction mixture (2 phases) is stirred at 25° C. for 60 h. The mixture is diluted with ethyl acetate (EtOAc) (200 mL) and slowly dropped into a solution of $K_2CO_3$ (50 g) in water (400 mL) at 5° C. The organic layer is separated and the aqueous layer washed with EtOAc (150 mL). The combined organic extracts are dried over $Na_2SO_4$ (10 g) and filtered. A solution of toluenesulfonic acid (TsOH) (7.6 g monohydrate in EtOAc (50 mL) is slowly added at 25° C. The white solid product is filtered after 30 min, washed and dried to give cis DTTT containing 5% trans. Two crystallizations from $CH_3CN$ (400 mL) gives 13.5 g pure (2R,4S)-DTTT (50% yield) $[a]_D^{25}$=+16.6° (c=1, MeOH); ee=99.6%.

Preparation of (−)-(2S,4R)-2-(2,4-Dichlorophenyl)-2-(1H-1,2,4-triazol-1-ylmethyl)-4-tosyloxymethyl-1,3-dioxolane tosylate DTTT (3b Tosylate Salt)

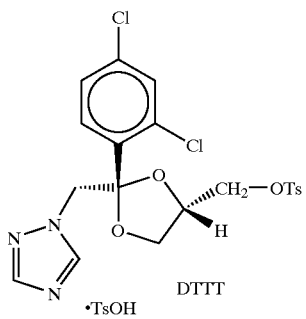

3b

A suspension of (S)-tosyloxy-1,2-propanediol (14.8 g, 60 mmol) and 1-(2,4-dichlorophenyl)-2-(1H-1,2,4-triazol-1-yl) ethanone (15.2 g, 58 mmol) in toluene (80 mL) is cooled to 5° C. Triflic acid (18 mL) is slowly added so that the temperature stays below 15° C. After complete addition the reaction mixture (2 phases) is stirred at 25° C. for 60 h. The mixture is diluted with $CH_2Cl_2$ (300 mL) and slowly dropped in a solution of $K_2CO_3$ (30 g) in water (300 mL) at 5° C. the organic layer is separated and concentrated to about 100 mL. The residue is diluted with methyl isobutylketone (MIBK) (300 mL) and a solution of TsOH (11.0 g monohydrate) in MIBK (100 mL) is slowly added at 25° C. The white solid product is filtered after 30 min., washed and dried to give cis DTTT containing 6% trans. Two crystallizations from $CH_3CN$ (600 mL) gives 16.6 g pure (2S,4R)-DTTT (44% yield).

$[\alpha]_D^{25}$=−16.6° (c=1, MeOH) ee=99.6%

Preparation of Meso-4,5-Dimethyl-1,2,3-dioxathiolane 2,2-Dioxide (5)

A three-necked 500 mL round-bottom flask fitted with a reflux condenser and a calcium chloride drying tube was charged with meso-2,3-butanediol (10.0 g, 10.1 mL, 0.11 mol) and carbon tetrachloride (20 mL). Thionyl chloride (15.98 g, 9.8 mL, 0.134 mol) was added dropwise at room temperature. Rapid gas evolution began. The reaction mixture was stirred at room temperature for 10 min, then warmed to reflux for 30 min to insure complete removal of HCl gas. The reaction mixture was cooled to 0° C. in an ice-water bath and acetonitrile (120 mL), RuCl3 H2O (14 mg, 0.07 mmol), NaIO4 (35.6, 0.166 mol) and water (180 mL) were added, respectively. The reaction mixture was allowed to warm to room temperature and stirred for 1.5 hr. The mixture was poured into methyl t-butyl ether (900 mL) and water was added to dissolve the remaining NaIO4 (ea. 600 mL). The phases were separated and the aqueous phase was extracted with methyl t-butyl ether (2×100 mL). The combined organic phases were washed with water (1×50 mL), saturated aqueous sodium bicarbonate (2×50 mL) and saturated aqueous sodium chloride (1×50 mL). The organic solution was dried over anhydrous magnesium sulfate and filtered through a bed of silica gel to give a clear and colorless solution. the solvent was removed in vacuo to give 16.20 g (96% yield) of the title compound.

Preparation of (4R,SR)-4,5-Dimethyl-1,2,3-dioxathiolane 2,2-Dioxide (5a)

A three-necked 500 mL round-bottom flask fitted with a reflux condenser and a calcium chloride drying tube was charged with (2R,3R)-(+)-2,3-butanediol (10.0 g, 10.1 ml, 0.11 mol) and carbon tetrachloride (120 mL). Thionyl chloride (16.0 g, 9.8 mL, 0.13 mol) was added dropwise at room temperature. Rapid gas evolution began. The reaction mixture was stirred at room temperature for 10 min, then warmed to reflux for 30 min to insure complete removal of HCl gas. The reaction mixture was cooled to 0° C. in an ice-water bath and acetonitrile (120 mL), RuCl3 H2O (14 mg, 0.07 mmol), NaIO4 (35.6 g, 0.17 mol) and water (180 mL) were added, respectively. The reaction mixture was allowed to warm to room temperature and stirred for 1.5 hr. The mixture was poured into methyl t-butyl ether (900 mL), and water was added to dissolve the remaining NaIO4 (ca. 600 mL). The phases were separated and the aqueous phase was extracted with methyl t-butyl ether (2×100 mL). The combined organic phases were washed with water (1×50 mL), saturated aqueous sodium bicarbonate (2×50 mL) and saturated aqueous bicarbonate (2×50 mL) and saturated aqueous sodium chloride (1×50 mL). The organic solution was dried over anhydrous magnesium sulfate and filtered through a bed of silica gel to give a clear and colorless solution. The solvent was removed in vacuo to give 16.01 g (95% yield) of the title compound.

Preparation of Potassium (2R*,3R*)-3-[2,4-Dihydro-4-[4-[4-(4-methoxyphenyl]-1-piperazinyl] phenyl]-3H-1,2,4-triazol-3-on-2-yl]but-2-yl Sulfate (7)

To a suspension of potassium hydride (8.53 g, 74.4 mmol, 35% dispersion in oil), prewashed with hexane (2×50 mL) in N,N-dimethylformamide (120 mL) at room temperature was added 18-crown-6 (15.73 g, 59.5 mmol) and 2,4dihydro-4-[4-[4-(4-methoxyphenyl)-1-piperazinyl] phenyl]-3-H-1,2,4-triazol-3-one (6)(17.43 g, 49.6 mmol). The solution was warmed to 80–85° C. for 1.5 hr, then cooled in an ice-water bath to 9° C. To this solution was added (4R*,5S*)-4,5-dimethyl-1,2,3-dioxathiolane 2,2-dioxide (5) (8.00 g, 52.6 mmol). The reaction mixture exothermed to 13° C. After recooling to 0° C., the reaction mixture was warmed to room temperature and stirred for 18 hr. The mixture was poured into 2.5 L of methyl t-butyl ether, and the solid product was filtered from the solution. Water (1 L) was added to the crude solid, and the mixture was warmed to 80° C. and the solid by-product was removed by filtration. The solid was rinsed with water (400 mL), and the filtrate was allowed to cool to room temperature. Saturated aqueous potassium chloride (50 mL) was added and the product precipitated from the solution immediately. After filtration, the solid was dried in vacuo to give 13.46 a (47% yield) of the title compound.

Preparation of Racemic 2,4-Dihydro-4-[4-[4-(4-hydroxyphenyl)-1-piperazinyl]phenyl]-2-[(1S*, 2R*)-2-hydroxy-1-methylpropyl)]-3H-1,2,4-triazol-3-one (8)

To potassium (2R*,3R*)-3-[2,4-Dihydro-4-[4-[4(4-methoxyphenyl)-1-piperazinyl]phenyl]-3H-1,2,4triazol-3- on-2-yl]but-2-yl sulfate (7) (7.00 g, 12.9 mmol) and sodium sulfite (480 mg, 3.80 mmol) was added 48% HBr (40 mL). The solution was heated to reflux for 6 hr, then cooled to room temperature. The reaction mixture was poured into water (100 mL) and the pH raised to 7–8 with saturated aqueous potassium carbonate solution. The product was collected by filtration and dried in vacua. The filtrate was extracted with chloroform (3×20 mL), and the combined organic fractions were dried over anhydrous magnesium sulfate, filtered and the solvent removed in vacuo to give a white solid. The solids were combined to give 3.89 g (62% yield) of the title compound as an adduct with $SO_3$.

Preparation of (2R,4S)-4-[4-[4-[4-[[2-(2,4-Dichlorophenyl)-2-(1H-1,2,4-triazole-1-ylmethyl)-1, 3-dioxolan-4-yl]methoxy]phenyl]-[-piperazinyl [phenyl]-2,4dihydro-2-[(1R*,2R*)-(2-hydroxy-1-methylpropyl)]-3H -1,2,4-triazol-3-one (Diastereomeric Mixture Containing A)

To 2,4-dihydro-4[4-[4-(4-hydroxyphenyl)-1-piperazinyl] phenyl]-2[(1R*,2R*)-(2-hydroxyl-1-methylpropyl)]-3H-1, 2,4-triazol-3-one $SO_3$ adduct (8) (1.00 g, 2.04 mmol) and (−)-(2R4S)-2-(2,4-dichlorophenyl)-2-(1H-1,2,4-triazol-1-ylmethyl)-4-tosylocxymethyl-1,3-dioxolane tosylate (3a tosylate) (1.52 g, 2.32 mmol) was added powdered potassium hydroxide (658 mg, 11.7 mmol) and N,N-dimethylformamide (30 mL). The reaction mixture was warmed to 50–55° C. for 8 hr and cooled to room temperature. Water was added (300 mL), and the mixture was stirred for 30 min. Saturated aqueous sodium chloride (50 mL) was added to the mixture, the mixture was stirred for 1 hr and the crude product was collected by filtration and dried in vacuo. Purification by flash chromatography, eluting with ethyl acetate, followed by chloroform, 98:2 chloroform:methanol, then 95:5 chloroform:methanol gave 420 mg (29% yield) of the title compound; $[\alpha]_D^{25}$=19.7° (c=0.1, MeOH).

Preparation of (2S,4R)-4-[4-[4-[4-[[2-(2,4-Dichlorophenyl)-2-(1H-1,2,4,-triazole-1-ylmethyl)-1,3-dioxolan-4-yl}methoxy]phenyl]-1-piperazinyl] phenyl]-2,4-dihydro-2-[(1R*,2R*)-(2-hydroxy-1-methylpropyl)-3H-1,2,4-triazol-3-one (Diastereomeric Mixture Containing B)

To 2,4 -dihydro-4-[4-[4(4-hydroxyphenyl)-1-piperazinyl] phenyl]-2-[(1R*,2R*)-2-hydroxy-1-methylpropyl)]-3H-1,2, 4-triazol-3-one (8) (1.00 g, 2.04 mmol) and (−)-(2S,4R)-2-(2,4dichlorophenyl)-2-(1H-1,2,4triazol-1-ylmethyl)-4-tosyloxymethyl-1,3-dioxolane tosylate (3b tosylate) (1.02 g, 1.56 mmol) was added powdered potassium hydroxide (428 mg, 7.63 mmol) and N,N-dimethylformamide (22 mL). The reaction mixture was warmed to 50–55° C. for 7 hr and cooled to room temperature. Water was added (220 mL) and the crude product was collected by filtration and dried in vacuo. Purification by flash chromatography, eluting with 98:2 chloroform:methanol, and recrystallization from methanol gave 388 mg (23% yield) of the title compound; $[\alpha]_D^=$=−18.5° (c=0.1, MeOH).

The compounds in which $X^1$ and $X^2$ are fluorine may be made in analogous fashion from the appropriate 3, which is available by condensation as shown in Scheme 1 from the appropriate 2,4-dihalophenylethanone.

The term "substantially pure single enantiomer" as used herein means that less than 10% by weight of other enantiomers is present. The compositions contain hydroxyitraconazole or a derivative thereof, in which at least 90% by weight of the hydroxyitraconazole has a cis dioxolane and a sec-butyl side chain of the stereochemistry shown above.

Microbiological and pharmacologic studies can be used to determine the relative potency and the profile of specificity of the optically pure enantiomers, and the racemic mixture of itraconazole as antimycotic agents with a broad spectrum of activity against many fungi, yeast, and dermatophytes.

With respect to antimicrobial activity of the aforementioned compounds, selected experiments are illustrated to profile useful antimicrobial activity, and not to limit this invention in any way, including the scope of susceptible microorganisms. Antifungal conazoles may be evaluated in vitro at several concentrations (in µg/mL) against a number of fungi and bacteria. [See, Van Cutsem *Chemotherapy* 38 *Suppl* 1, 3–11 (1992) and Van Cutsem et al. *Rev. Infec. Dis.* 9 *Suppl*1, S15–S32 (1987)]. The fungistatic assay is carried out in Sabouraud's liquid (1 g of neopeptone Difco and 2 g of glucose Difco per 100 mL of distilled water) in 16×160 mm test tubes, each containing 4.5 mL of liquid medium which has been autoclaved at 120° for 5 min. The compounds to be tested are dissolved in 50% alcohol at initial concentration of 20 mg/mL. The solutions are subsequently diluted with sterile distilled water to give a concentration of 10 mg/mL. Successive decimal dilutions are made in distilled water. To tubes containing 4.5 mL of Sabouraud's liquid medium 0.5 mL of the solution of the drug is added, thereby obtaining concentrations of 1000, 500, 100, 10, and 1 µg/mL of medium. Control tubes are prepared by adding 0.5 mL of distilled water to 4.5 of mL medium, alcohol being added to give concentrations identical with the tubes containing 1000 and 500 µg of the drug. The filamentous fuingi are incubated in Sabouraud's agar at 25° for 2–3 weeks. A block of 2×2×2 mm is then inoculated into the medium. All cultures are made in duplicate and are incubated at 25° for 14 days. Itraconazole antifungal activity is enhanced in vitro in Sabouraud broth containing 10% inactivated bovine serum, and depends on the test medium used. Complete or marked inhibition of growth in Sabouraud broth after 14 days of incubation may be observed with *Microsporum canis, Trichophyton mentagrophytes, Candida albicans, Sporothrix schenckii, Paracoccidioides brasiliensis, Blastomyces dermatitides*, Histoplasma spp., Aspergillus spp. and other fungi and bacteria.

A 10 mL tube containing 4 mL of Sabourauds dextrose broth was inoculated with 1 colony of Candida albicans picked from a plate of pure culture. The strain was ordered from the American Type Culture Collection (ATCC). The organism was grown for 4 hours at 30° C. while shaking at 150 RPM. While the organism was growing, samples of the diastereomeric mixtures 9 containing hydroxy-itraconazoles A and B were solubilized to a concentration of 10 mg/mL in DMSO. Each sample was then diluted 1:10 to make 1 mg/mL samples or 1000 µg/mL. These samples were then diluted by serial 2-fold dilutions to produce samples now containing 1000, 500, 250, 125, 62.5, 31.25, 15.6 µg/mL. A 96-well microtiter dish was set up with 98 µL of liquid growth media in each test well, along with 1 µL of hydroxy-itraconazole solution. At 4 hours of growth time the *Candida albicans* was diluted to a 0.5 McFarland standard representing about $10^5$–$10^6$ cells/mL and 1 µL of this inoculum placed into each test well of the microtiter dish. The dish was then covered and incubated at 30° C. for 16 hours. The MIC's for both mixtures containing A and B were below 0.156 µg/mL.

Kirby-Bauer Testing

Actively growing cultures of *Candida albicans, Cryptococcus neoformens* and *Saccharomnyces cerevisiae* were prepared as described above. The cultures were diluted to a 0.5 McFarland standard and swabbed onto a 150 mm Sabouraud Dextrose agar plates. Paper disks (7 mm) were placed onto the agar plates using a disk dispenser. Next 10 µl of 10 mg/mL solutions of each sample hydroxyitraconazole was pipetted onto separate paper disks. The plates were then incubated at 30° C. for 16 hours. Zones of inhibition were then measured in mm.

The data are summarized below.

| Compound | Candida albicans | Cryptococcus neoformens | Saccharomyces cerevisae |
| --- | --- | --- | --- |
| A diastereomer | 23 | 34 | 23 |
| B diastereomer | 27 | 32 | 25 |
| ± Itraconazole | 17 | 22 | 15 |

Data Represent Zones of Inhibition in mm.

In vivo activity of hydroxyitraconazole and derivatives may be compared against experimental cutaneous candidosis in guinea pigs, and vaginal candidosis in rats. The in vivo activity of the compounds in vaginal candidosis is evaluated by inducing vaginal infection with C. albicans in ovariectomized and hysterectomized Wistar rats (100 g) which are treated weekly with 100 µg of estradiol undecanoate in sesame oil, subcutaneously. Animals in pseudooestrus are infected intravaginally with a fixed concentration of C. albicans in saline. Control of infection or cure is estimated by taking vaginal smears at fixed days after infection. Drugs to be evaluated, and compared on a mg/kg basis, may be given prophylactically, or therapeutically and their efficacy judged by comparison the ratio of negative animals to the total number in each drug group. In similar studies, the activity against cutaneous candidosis in guinea pigs [(Van Cutsem et al. *Chemotherapy* 17, 392, (1972)] provides the basis of comparison.

The compounds of the present invention allow the treatment of fungal infections while avoiding the adverse effects associated with itraconazole. The term "adverse effects" includes, but is not limited to, arrhythmogenicity, hepatotoxicity and elevations in serum liver enzymes, drug interactions, hypersensitivity reactions including urticaria, nausea, vomiting, abdominal pain, headache, dizziness and the like.

The potential for promoting arrhythmia is evaluated by examining the effects of the isomers of hydroxyitraconazole on cardiac action potential and contractility in human, canine and rabbit hearts. Torsades de Pointes is a well known side effect of antiarrhythmic drugs, such as quinidine, sotalol and acetyl-procainamide, which cause a prolongation of cardiac repolarization. All of these drugs have in common the ability to block a cellular potassium channel called the delayed rectifier ($I_K$), and it is generally assumed that this is mechanistically linked to their ability to induce the syndrome of Torsades de Pointes. [See, Zehender et al. *Cardiovascular Drugs Ther.*, 5 515–530 (1991).] Increases in QT duration and action potential duration in isolated guinea pig or rabbit hearts can therefore be used to indicate an arrhythmogenic effect. Hearts are perfused with an oxygenated Tyrode's solution, containing 0.0; 1.0; 5.0; 10.0 or 30.0 µM of racemic itraconazole. QT duration and action potential duration (APD) are measured from cardiac electrodes.

To observe the effects in viv, mongrel dogs of either sex weighing 5–20 kg are anesthetized and instrumented by standard techniques for blood pressure and EKG. A solid state transducer for dP/dT is placed in the left cardiac ventricle, and an epicardial electrode is put into place. The test compound is infused at progressively higher doses, beginning at 1 µg/kg/min for 15 to 30 minutes and increased incrementally until a cardiovascular collapse ensues. Parameters measured are: blood pressure, heart rate, dP/dT, and the QT-interval. Measurements of hemodynamics and electrical activity, including QTc interval, are made in response to the test compound and compared.

The potential for promoting hepatotoxicity is assessed in vitro in human hepatic microsomes, human lymphocytes or other cell culture systems. Hepatic microsomes are prepared from human liver. Tissue is thawed and then homogenized in 0.15 M KCl in a Polytron homogenizer. The homogenate is centrifuged and the pellet is resuspended and homogenized in 0.15 M KCl. Aliquots are frozen and stored at −70° C. Human lymphocytes are aseptically isolated from fresh, heparinized human blood. Blood is diluted with Eagle's minimal essential medium and layered on Ficoll-Paque. The samples are centrifuged, and lymphocytes are then removed from the aqueous-Ficoll interface and suspended in medium (15 Mm HEPES, pH, 7.4). The cells are then centrifuged, washed once in the HEPES medium, and resuspended.

Cytotoxicity is assessed by the conversion of 3-(4,5 dimethylthiazol-2-yl)-2,5-diphenyltetrazolium bromide (MMT) to a purple formazan. The conversion of MTT to dye is done in multiwell plates. After preparation, hepatic microsomes or lymphocytes are incubated alone or with the test compound in a concentration range from 1 to 400 µM at 37° C. in a humidified incubator. After incubation, the microsomes/cells are washed with 5% albumin in HEPES-buffered medium and resuspended. The microsomes/cells are then incubated at 37° C. in a humidified incubator. After the incubation, 125 µg of MTT is added to each well. The plates are incubated at 37° C. and centrifuged. After centrifugation, 100 µL of isopropanot is added and, after incubation, the optical density is determined using an automated plate-reader.

The magnitude of a prophylactic or therapeutic dose of hydroxyitraconazole or derivative in the acute or chronic management of disease will vary with the severity of the condition to be treated, and the route of administration. The dose, and perhaps the dose frequency, will also vary according to the age, body weight, and response of the individual patient. In general, the total daily dose range, for hydroxyitraconazole or a derivative, for the conditions described herein, is from about 50 m to about 1200 mg, in single or divided doses. Preferably, a daily dose range should be between about 100 mg to about 800 mg, in single or divided doses, while most preferably, a daily dose range should be between about 200 mg and 400 mg, in divided doses. In managing the patient, the therapy should be initiated at a lower dose, perhaps about 100 mg to about 200 mg, and increased up to about 400 mg or higher depending on the patient's global response. It is further recommended that children, and patients over 65 years, and those with impaired renal, or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. An amount sufficient to alleviate or prevent infections but insufficient to cause adverse effects is encompassed by the above-described dosage amounts and dose frequency schedule.

Any suitable route of administration may be employed for providing the patient with an effective dosage of hydroxyitraconazole or derivative. For example, oral, rectal, parenteral (subcutaneous, intramuscular, intravenous), transdermal, topical and like forms of administration may be employed. Dosage forms include tablets, troches, dispersions, suspensions, solutions, capsules, patches, ointments, creams, shampoos and the like.

The pharmaceutical compositions of the present invention comprise hydroxyitraconazole or derivative as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the hydroxy compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like. The phosphate and sulfate, being acidic, allow for the preparation of salts of bases as well as internal salts. Suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The compositions of the present invention include compositions such as suspensions, solutions, elixirs, aerosols, and solid dosage forms. Carriers such as starches, sugars, microcrystalline cellulose, diluents, granulating agents, lubricants, binders, disintegrating agents, and the like, are commonly used in the case of oral solid preparations (such as powders, capsules, and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

A second preferred route of administration is topically, for which creams, ointments, shampoos, and the like are well suited.

In addition to the common dosage forms set out above, the compounds of the present invention may also be administered by controlled release means and/or delivery devices and, because of their solubility, may also be employed in parenteral solutions, such as for intravenous administration.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent Molded tablets may be made by molding in a suitable machine, a mixture of the powdered compound moistened with an inert liquid diluent. Desirably, each tablet contains from about 100 mg to about 300 mg of the active ingredient. Most preferably, the tablet, cachet or capsule contains either one of three dosages, about 50 mg, about 100 mg, or about 200 mg of the active ingredient.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The invention is further defined by reference to the following examples describing in detail the preparation of the compositions of the present invention as well as their utility. It will be apparent to those skilled in the art that many modifications, both to materials and methods may be practiced without departing from the purpose and interest of this invention.

EXAMPLE 1

Oral Formulation—Capsules

|  | Quantity per capsule in mg | | |
|---|---|---|---|
| Formula | A | B | C |
| Hydroxyitraconazole | 50 | 100 | 200 |
| Lactose | 380 | 330 | 230 |
| Cornstarch | 65 | 65 | 65 |
| Magnesium Stearate | 5 | 5 | 5 |
| Compression Weight | 500 | 500 | 500 |

The active ingredient, hydroxyitraconazole or derivative, is sieved and blended with the excipients. The mixture is filled into suitably sized two-piece hard gelatin capsules using suitable machinery. Other doses may be prepared by altering the fill weight and if necessary, changing the capsule size to suit.

EXAMPLE 2

Oral Formulation—Tablets

|  | Quantity per tablet in mg | | |
| --- | --- | --- | --- |
| Formula | A | B | C |
| Hydroxyitraconazole | 50 | 100 | 200 |
| Lactose | 109 | 309 | 209 |
| Cornstarch | 30 | 30 | 30 |
| Water (per thousand tabs)* | 300 mL | 300 mL | 300 mL |
| Cornstarch | 60 | 60 | 60 |
| Magnesium Stearate | 1 | 1 | 1 |
| Compression Weight | 250 | 500 | 500 |

*The water evaporates during manufacture

The active ingredient is blended with the lactose until a uniform blend is formed. The smaller quantity of cornstarch is blended with the water to form the resulting cornstarch paste. This is then mixed with the uniform blend until a uniform wet mass is formed and the remaining cornstarch is added and mixed until uniform granules are obtained. The granules are screened through a suitable milling machine using a ¼" stainless steel screen. The milled granules are dried in a suitable drying oven and milled through a suitable milling machine again. The magnesium stearate is then blended and the resulting mixture is compressed into tablets of desired shape, thickness, hardness and disintegration.

We claim:

1. A 1:1 mixture of isomers of formulae:

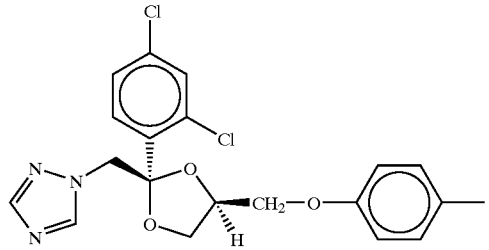

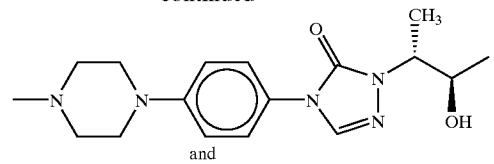

and

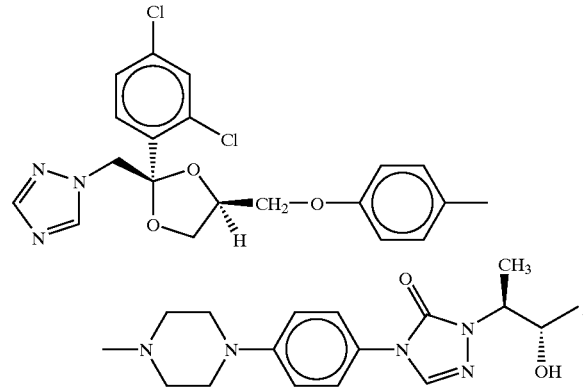

or a salt thereof.

2. A pharmaceutical composition comprising a mixture according to claim 1, and a pharmaceutically acceptable carrier.

3. A pharmaceutical composition according to claim 2, wherein said pharmaceutically acceptable carrier comprises a carrier for parenteral administration.

4. A pharmaceutical composition according to claim 2, wherein said pharmaceutically acceptable carrier comprises a carrier for controlled release administration.

* * * * *